(12) United States Patent
Mohan et al.

(10) Patent No.: US 8,506,983 B2
(45) Date of Patent: *Aug. 13, 2013

(54) BONE FILLER MATERIAL

(75) Inventors: Suneeth Elizabeth Mohan, Memphis, TN (US); Daniel Andrew Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 385 days.

This patent is subject to a terminal disclaimer.

(21) Appl. No.: 12/818,322

(22) Filed: Jun. 18, 2010

(65) Prior Publication Data

US 2010/0255115 A1  Oct. 7, 2010

Related U.S. Application Data

(63) Continuation-in-part of application No. 12/695,925, filed on Jan. 28, 2010, which is a continuation-in-part of application No. 11/415,036, filed on May 1, 2006, now Pat. No. 7,771,741.

(51) Int. Cl.
*A61F 2/28* (2006.01)

(52) U.S. Cl.
USPC .......................................... 424/423; 424/488

(58) Field of Classification Search
USPC ................................................ 424/423, 488
See application file for complete search history.

(56) References Cited

U.S. PATENT DOCUMENTS

| | | |
|---|---|---|
| 4,394,370 A | 7/1983 | Jeffries |
| 4,430,760 A | 2/1984 | Smestad |
| 4,440,750 A | 4/1984 | Glowacki et al. |
| 4,472,840 A | 9/1984 | Jefferies |
| 4,485,097 A | 11/1984 | Bell |
| 4,517,216 A | 5/1985 | Shim |
| 4,722,948 A | 2/1988 | Sanderson |
| 4,789,663 A | 12/1988 | Wallace et al. |
| 4,863,732 A | 9/1989 | Nathan et al. |
| 5,124,273 A | 6/1992 | Minami |
| 5,162,114 A | 11/1992 | Kuberasampath et al. |
| 5,273,964 A | 12/1993 | Lemons |
| 5,275,954 A | 1/1994 | Wolfinbarger et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |
| 5,356,629 A | 10/1994 | Sander et al. |
| 5,405,390 A | 4/1995 | O'Leary et al. |
| 5,439,684 A | 8/1995 | Prewett et al. |
| 5,510,396 A | 4/1996 | Prewett et al. |
| 5,513,662 A | 5/1996 | Morse et al. |
| 5,516,532 A | 5/1996 | Atala et al. |
| 5,531,791 A | 7/1996 | Wolfinbarger, Jr. |
| 5,707,962 A | 1/1998 | Chen et al. |
| 5,711,957 A | 1/1998 | Patat et al. |
| 5,811,401 A | 9/1998 | Bucala et al. |
| 5,869,527 A | 2/1999 | Fang et al. |
| 5,948,426 A | 9/1999 | Jeffries |
| 5,972,385 A | 10/1999 | Liu et al. |
| 6,030,635 A | 2/2000 | Gertzman et al. |
| 6,117,979 A | 9/2000 | Hendriks et al. |
| 6,124,273 A | 9/2000 | Drohan et al. |
| 6,165,487 A | 12/2000 | Ashkar et al. |
| 6,180,606 B1 | 1/2001 | Chen et al. |
| 6,197,325 B1 | 3/2001 | MacPhee et al. |
| 6,200,606 B1 | 3/2001 | Peterson et al. |
| 6,214,368 B1 | 4/2001 | Lee et al. |
| 6,261,586 B1 | 7/2001 | McKay |
| 6,281,195 B1 | 8/2001 | Rueger et al. |
| 6,287,341 B1 | 9/2001 | Lee et al. |
| 6,293,970 B1 | 9/2001 | Wolfinbarger et al. |
| 6,294,041 B1 | 9/2001 | Boyce et al. |
| 6,294,187 B1 | 9/2001 | Boyce et al. |
| 6,297,213 B1 | 10/2001 | Oppermann et al. |
| 6,309,659 B1 | 10/2001 | Clokie |
| 6,311,690 B1 | 11/2001 | Jeffries |
| 6,326,018 B1 | 12/2001 | Gertzman et al. |
| 6,328,765 B1 | 12/2001 | Hardwick et al. |
| 6,331,312 B1 | 12/2001 | Lee et al. |
| 6,340,477 B1 | 1/2002 | Anderson |

(Continued)

FOREIGN PATENT DOCUMENTS

| | | |
|---|---|---|
| RU | 219797 C1 | 2/2003 |
| WO | WO 9639203 | 12/1996 |
| WO | WO0236147 A1 | 5/2002 |
| WO | WO 0245765 | 6/2002 |
| WO | WO02008322 A1 | 11/2002 |
| WO | WO03020327 A2 | 3/2003 |
| WO | WO 03030956 | 4/2003 |
| WO | WO2005011764 A1 | 2/2005 |

OTHER PUBLICATIONS

Eskandari, M.M. etal. (2006). "In vitro re-mineralization of demineralized bone matrix in human serum." Clin Chem Lab Med. 2006;44(1):54-8.

Lee, Kenneth J.H. et al. (2005) "Demineralized bone matrix and spinal arthrodesis" The Spine Journal (5): 217S-223S.

Pacaccio, D. J., et al. (2005). Demineralized bone matriz: basic science and clinical applications. Clin Podiatr Med Surg North Am. Oct. 2005; 22(4): 599-606, vii.

Peitrzak, W.S., et al. (2005) "Demineralized bone matrix graft: a scientific and clinical case study assessment." J Foot Ankle Surg. Sep.-Oct. 2005, . .(5):345-53.

(Continued)

*Primary Examiner* — Taeyoon Kim
(74) *Attorney, Agent, or Firm* — Sorell Lenna & Schmidt LLP

(57) ABSTRACT

Described are bone generation matrixes having an admixture of demineralized bone matrix (DBM) particles and/or bone chips in combination with at least one binding agent selected from the group consisting of alginate, lectin, pectin, gellan gum, starch, collagen and combinations thereof in an aqueous solvent, wherein the DBM particles and/or bone chips are present in an amount of at least 65% by dry weight and the ratio of the aqueous solvent to the dry weight of the DBM particles/bone chips and at least one binding agent is between about 1:1 to about 1:6.

13 Claims, No Drawings

(56) References Cited

U.S. PATENT DOCUMENTS

| | | | |
|---|---|---|---|
| 6,346,515 | B1 | 2/2002 | Pitaru et al. |
| 6,368,356 | B1 | 4/2002 | Zhong et al. |
| 6,372,257 | B1 | 4/2002 | Marchosky |
| 6,437,018 | B1 | 8/2002 | Gertzman et al. |
| 6,444,252 | B1 | 9/2002 | Gordon et al. |
| 6,444,254 | B1 | 9/2002 | Chilkoti et al. |
| 6,458,375 | B1 | 10/2002 | Gertzman et al. |
| 6,576,015 | B2 | 6/2003 | Geistlich et al. |
| 6,576,016 | B1 | 6/2003 | Hochshuler et al. |
| 7,045,141 | B2 | 5/2006 | Merboth et al. |
| 7,122,057 | B2 | 10/2006 | Beam et al. |
| 7,163,691 | B2 | 1/2007 | Knaack et al. |
| 7,291,345 | B2 | 11/2007 | Winterbottom et al. |
| 2001/0014667 | A1 | 8/2001 | Chen et al. |
| 2001/0018614 | A1 | 8/2001 | Bianchi |
| 2001/0043940 | A1 | 11/2001 | Boyce et al. |
| 2002/0018796 | A1 | 2/2002 | Wironen et al. |
| 2002/0034531 | A1 | 3/2002 | Clokie |
| 2002/0071827 | A1 | 6/2002 | Petersen et al. |
| 2002/0072804 | A1 | 6/2002 | Donda |
| 2002/0076429 | A1 | 6/2002 | Wironen |
| 2002/0082697 | A1 | 6/2002 | Damien |
| 2002/0090725 | A1 | 7/2002 | Simpson et al. |
| 2002/0107570 | A1 | 8/2002 | Sybert et al. |
| 2002/0151985 | A1 | 10/2002 | Kuberasampath et al. |
| 2002/0197242 | A1 | 12/2002 | Gertzman et al. |
| 2003/0143258 | A1* | 7/2003 | Knaack et al. ............ 424/426 |
| 2003/0206937 | A1 | 11/2003 | Gertzman et al. |
| 2004/0097612 | A1 | 5/2004 | Rosenberg et al. |
| 2005/0020506 | A1 | 1/2005 | Drapeau et al. |
| 2006/0030948 | A1 | 2/2006 | Manrique et al. |
| 2007/0254041 | A1 | 11/2007 | Drapeau et al. |
| 2009/0130173 | A1 | 5/2009 | Behnam et al. |
| 2009/0142385 | A1* | 6/2009 | Gross et al. ............... 424/422 |
| 2009/0220605 | A1 | 9/2009 | Wei et al. |

OTHER PUBLICATIONS

Lee, Yo-Po, et al. (2005). "The efficacy of difference commercially available demineralized bone matrix susbtances in an athymic rat model." J Spinal Disord Tech. 2005;18:439-444.

Ranly, Don M., DDS, et al. (2005). "Platelet-derived growth factor inhibits demineralized bone matrix-induced intramuscular cartilage and bone formation." The Journal of Bone of Joint Surgery, Inc., JBJS.org, Sep. 2005; vol. 87-A, No. 9, 2052-64.

Ziran, B., et al. (2005). "Comparative efficacy of 2 different demineralized bone matrix allografts in treating long-bone nonunions in heavy tobacco smokers." Am J Orthop. Jul. 2005;34(7):329-32.

Han, Bo, et al. (2005). "Effect of moisture and temperature on the osteoinductivity of demineralized bone matrix." Journal of Orthopaedic Research, 23 (2005) 855-861.

Colnot, Celine, Ph.D, et al. (2005). "Mechanisms of action of demineralized bone matrix in the repair of cortical bone defects." Clinical Orthopaedics and Related Research, Jun. 2005, No. 435:69-78.

Bender, Sa, et al. (2005). "Evaluation of demineralized bone matrix paste and putty in periodontal intraosseous defects." J Periodontol. May 2005;76(5):768-77.

Schouten, C.C., et al. (2005) "DBM induced ectopic bone formation in the rat: The importance of surface area." Journal of Materials Science: Materials in Medicine, 16(2005)149-152.

Peterson, Brett, MD, etal. (2004). "Osteoinductivity of commercially available demineralized bone matrix." The Journal of Bone and Joint Surgery, Inc., JBJS.org, Oct. 2004; vol. 86-A, No. 10, 2243-50.

Bomback, David A., MD, et al. (2004). "Comparison of posterolateral lumbar fusion rates of grafton putty and OP-1 putty in an athymic rat model." Spine.2004, vol. 29, No. 15, 1612-1617.

Hartman, Ed H.M., MD, etal. (2004). "Demineralized bone matrix-induced ectopic bone formation in rats: In Vivo study with follow-up by Magnetic Resonance Imaging, Magnetic Resonance Angiography, and Dual-Energy X-Ray Absorptiometry." Tissue Engineering. vol. 10, No. 5/6, 2004, 747-754.

Traianedes, Kathy, et al. (2004). "Donor age and gender effects on osteoinductivity of demineralized bone matrix." J Biomed Mater Res B Appl Biomater. Jul. 15, 2004:70(1):21-9.

Klepp, M, et al. (2004). "Histologic evaluation of demineralized freeze-dried bone allografts in barrier membrane covered periodontal fenestration wounds and ectopic sites in dogs." J Clin Periodontol. Jul. 2004;3 1(7):534-44.

Louis-Ugbo, John, et al. (2004). "Evidence of Osteoinduction by Grafton Demineralized Bone Matrix in Nonhuman Primate Spinal Fusion." Spine, 2004, vol. 29, No. 4, 360-366.

Cammisa, Frank P., Jr., et al. (2004). "Two-Year Fusion Rate Equivalency Between Grafton DBM Gel and Autograft in Posterolateral Spine Fusion." Spine, vol. 29, No. 6, 660-666.

Blum, B, et al. (2004). "Measurement of bone morphogenetic proteins and other growth factors in demineralized bone matrix." Orthopedics. Jan. 2004;27(1Suppl):s161-5.

Etienne, G., et al. (2004). "Use of cancellous bone chips and demineralized bone matrix in the treatment of acetabular osteolysis: preliminary 2-year follow-up." Orthopedics. Jan. 2004;27(1Suppl):s123-6.

Leatherman, DB, etal. (2004). "The use of demineralized bone matrix for mastoid cavity obliteration." Otol Neurotol. Jan. 2004;25(1):22-5; discussion 25-6.

Yee, Albert Juang Ming MD, et al. (2003). "Augmentation of Rabbit Posterolateral Spondylodesis Using a Novel Demineralized Bone Matrix-Hyaluronan Putty." Spine, vol. 28, No. 21, 2435-2440.

Stavropoulos A., et al. (2003). "Influence of demineralized bone matrix's embryonic origin on bone formation: an experimental study in rats." Clin Implant Dent Relat Res. 2003;5(3): 184-92.

Oaks, Daniel A., et al. (2003). "An Evaluation of Human Demineralized Bone Matrices in a Rat Femoral Defect Model." Clinical Orthopaedics and Related Research, No. 413, 281-290.

Han, Bo, et al. (2003). "Quantitative and sensitive in vitro assay for osteoinductive activity of demineralized bone matrix." Journal of Orthopaedic Research. 21 (2003)648-654.

Wilkins, RM, et al. (2003). "The effect of allomatrix injectable putty on the outcome of long bone applications." Orthopedics. May 2003;26(5Suppl):s565-70.

Turner, TM, et al. (2003). "Restoration of large bone defects using a hard-setting, injectable putty containing demineralized bone particles compared to cancellous autograft bone." Orthopedics. May 2003;26(5Suppl):s561-5.

Takikawa, Satoshi, et al. (2003). "Comparative evaluation of the osteoinductivity of two formulations of human demineralized bone matrix." J Biomed Mater Res A. Apr. 1, 2003;65(1):37-42. PM1D:12635152 [PubMed—indexed for Medline].

Cook, et al. (2002). "The effect of demineralized bone matrix gel on bone ingrowth and fixation of porous implants." J Arthroplasty. Jun. 2002;17(4):402-8. PMID: 12066267 [PubMed—indexed for Medline].

Dickman, Curtis A. (2001). Osteoinductive demineralized bone: what's the risk? Spine. Jul. 1, 2001;26(13):1409-10. No abstract available. PMID: 11458139 [PubMed—indexed for Medline].

Bostrom, MPG, et al. (2001). "An unexpected outcome during testing of commercially available demineralized bone graft materials." Spine, vol. 26, No. 13, 1425-1428.

Wang, Jeffrey C, et al. (2001). "Dose-Dependent toxicity of a commercially available demineralized bone matrix material." Spine, Jul. 1, 2001;26(13):1429-35;discussion 1435-6, PMID: 11458146 [PubMed—indexed for Medline].

Li H, et al. (2000), "Identification of bone morphogenetic proteins 2 and 4 in commercial demineralized freeze-dried bone allograft preparations: pilot study." Clin Implant Dent Relat Res. 2000;2(2):110-7. PMID: 11359264 [PubMed—indexed for Medline].

Maddox, Ewa, etal., (2000). "Optimizing human demineralized bone matrix for Clinical application." Tissue Eng. Aug. 2000:441-8. PMID: 10992439 [PubMed—indexed for MEDLINE].

Russell, James L., (2002). "Grafton Demineralized Bone Matrix: Performance Consistency, Utility, and Value." Tissue Engineering, vol. 6, No. 4, 2000; 435-440.

Russell, JL, et al, (1999). "Clinical utility of demineralized bone matrix for osseous defects, arthrodesis, and reconstruction: impact of processing techniques and Study methodology." Orthopedics. May 1999;22(5):524-31; quiz 532-3. Review. PMID: 10348114 [PubMed—indexed for MEDLINE].
Carnes, DL, et al., (1999). "Evaluation of 2 novel approaches for assessing the ability of demineralized freeze-dried bone allograft to induce new bone formation." J Periodontol. Apr. 1999;70(4):353-63. PMID: 10328645 [PubMed—indexed for MEDLINE].
Hagino, T., et al. (1999). "Accelerating bone formation and earlier healing after using demineralized bone matrix for limb lengthening in rabbits." J Orthop Res. Mar. 1999; 17(2):232-7. PMID: 10221840 [PubMed—indexed for MEDLINE].
Martin, George J., etal., (1999). "New formulations of demineralized bone matrix as a more effective graft alternative in experimental posterolateral lumbar spine arthrodesis." Spine. Apr. 1, 1999;24(7):637-45. PM1D:10209791 [PubMed—indexed for MEDLINE].
Garraway R., et al., (1998). "An assessment of the osteoinductive potential of commercial demineralized freeze-dried bone in the murine thigh muscle implantation model." J Periodontal. Dec. 1998;69(12):1325-36. PMID9926762 [PubMed—indexed for MEDLINE].
Edwards, JT., et al., (1998). "Osteoinduction of human demineralized bone:characterization in a rat model." ciin Orthop Reiat Res. Dec. 1998;( 357):2i9-28. PMID:9917720 [PubMed—indexed for MEDLINE].
Chesmel, KD, et al., (1998). "Healing response to various forms of human deminerlized bone matrix in athymic rat cranial defects." J Oral Maxiiiofac Surg. Jul. 1998;56(7):857-63; discussion 864-5. PMID: 9663577 [PubMed—indexed for MEDLINE].
Torricelli, P., etal., (1998). "In vitro osteoinduction of demineralized bone." Artif Cells Blood Substit Immobil Biotechnol. May 1998;26(3):309-15. PMID:9635123 [PubMed—indexed for MEDLINE].
Pinholt, EM, etal., (1998). "Osteoinductive potential of demineralized rat bone increases with increasing donor age from birth to adulthood." [PubMed—indexed for MEDLINE] nor age from birth to adulthood. J Craniofac Surg. Mar. 1998;9(2): 142-6. PMID:9586543.
Morone, Michael A., et al., (1998). "Experimental Posterolateral Lumbar Spinal Fusion With a Demineralized Bone Matrix Gel." Spine. vol. 23(2), Jan. 15, 1998, 159-167.
Zhang, M et al., (1997). "Effect(s) of the demineralization process on the osteoinductivity of demineralized bone matrix." J Peridonontai. Nov. 1997;68(11):1085-92. PMID: 9407401 [PubMed—indexed for Medline].
Caplanis, N. et al., (1997). "Effect of allogeneic, freeze-dried, demineralized bone matrix on guided bone regeneration in supra-alveolar per-implant defects in dogs." Int J Oral Maxiilofac Implants. Sep.-Oct. 1997;12(5):634-42. PMID:9337024 [PubMed—indexed for Medline].
Becerra, J., et al. (1996). "Demineralized bone matrix mediates differentiation of bone marrow stromal cells in vitro: effect of age of cell donor." J Bone Miner Res. Nov. 1996;11(11):1703-14. PMID: 8915778 [PubMed—indexed for Medline].
Rabie, AB, et al., (1996). "The effect of demineralized bone matrix on the healing of intramembranous bone grafts in rabbit skull defects." J Dent Res. Apr. 1996;75(4):1045-51. PMID 8708134 [PubMed—indexed for Medline].
Nyssen-Behets C, et al., (1996). "Aging effect on inductive capacity of human demineralized bone matrix." Arch Orthop Trauma Surg. 1996;115(6):303-6. PMID:8905101 [PubMed—indexed for Medline].
Feighan, JE., et al., (1995). "Induction of bone by a demineralized bone matrix gel: a study in a rat femoral defect model." PMID:8544025 [PubMed—indexed for Medline].
Zhang, M. et al., (1997). "A quantitative assessment of osteoinductivity of human demineralized bone matrix." J Peridononta. Nov. 1997;68(11):1076-84. PMID: 9407400 [PubMed—indexed for Medline].
Toba, Toshinari et al., "Regeneration of Canine Peroneal Nerve with the Use of a Polyglycolic Acid-Collagen Tube Filled with Laminin-Soaked Collagen Sponge: A Comparative Study of Collagen Sponge and Collagen Fibers as Filling Materials for Nerve Conduits," Japan Society for the Promotion of Science, Grant No. JSPS-RFTF 96100203 (2001).
Yarat, A. et al., "A method for preparing collagen graft materials," J. Marmara Univ. Dent. Fac, Sep. 1996; 2(2-3):527-9.
CH, Tsai et al., "A composite graft material containing bone particles and collagen in osteoinduction in mouse," J. Biomed Mater Res., 2002;63(1 ):65-70.
Friess, W. et al., "Effects of processing conditions on the rheological behavior of collagen dispersions," Eur. J. Pharm. Biopharm, May 2001; 51(3):259-65.
Doillon, C.J. et al., "Collagen-based wound dressings: control of the pore structure and morphology," J Biomed Mater Res, Oct. 1986, 20(8): 1219-28.
Dung, S.Z. et al., "Degradation of insoluble bovine collagen and human dentine collagen pretreated in vitro with lactic acid, pH 4.0 and 5.5," Arch. Oral Biol., Oct. 1994, 39(10):901-5.
Devore, D.P. et al., "Rapidly polymerized collagen gel as a smoothing agent in excimer laser photoablation," J. Refract. Surg., Jan.-Feb., 11(1):50-5.
Kumar, A.J. etal., "Preoperative embolization of hypervascular head and neck neoplasms using microfibrillar collagen," AJNR Am. J. Neuroradiol., Mar.-Apr. 1982, 3(2):163-8.
Zhang, L. et al., "The modification of scaffold material in building artificial dermis," Artif. Cells Blood Substit. Immobil. Biotechnol.. Jul. 2002. 30(4):319-32.
Olde Damink, L.H. et al., "Cross-linking of dermal sheep collagen using a water-soluble carbodiimide," Biomaterials, Apr. 1996, 17(8):765-73.
Lee, J.D. et al., "Characterization of UV-irradiated dense/porous collagen membranes: morphology, enzymatic degradation, and mechanical properties," Yonsei Med. J., Apr. 2001, 42(2): 172-9.
Pietrucha, K., "Effect of irradiation on collagen solutions in relation to biomedical applications," Polim. Med., 1989, 19(1-2):3-18.
Kuijpers, A.J. et al., "In vivo compatibility and degradation of crosslinked gelatin gels incorporated in knitted Dacron," J Biomed Mater Res, Jul. 2000, 51(1):135-45.
Weadock, K.S. et al., "Effect of physical crosslinking methods on collagen-fiber durability in proteolytic solutions," J Biomed Mater Res, Oct. 1996, 32(2):221-6.
Roche, S. et al., "Native and DPPA cross-linked collagen sponges seeded with fetal bovine epiphyseal chondrocytes used for cartilage tissue engineering," Biomaterials, 2001, 22:9-18.
Schoof, Heike et al., "Control of Pore Structure and Size in Freeze-Dried Collagen Sponges," J Biomed Mater Res, 2001, 58:253-357.
Quteish, D. et al., "Development and testing of a human collagen graft material," J Biomed Mater Res, Jun. 1990, 24(6):749-60.
Curtil, A. et al., "Freeze drying of cardiac valves in preparation for cellular repopulation," Cryobiology, Feb. 1997, 34(1): 13-22.
Wissink, M.J. et al., "Endothelial cell seeding on crosslinked collagen: effects of crosslinking on endothelial cell proliferation and functional parameters," Thromb. Haemost. Aug. 2000, 84(2):325-31.
Pokharna, H.K. et al., "Collagen crosslinks in human lumbar intervertebral disc aging," Seine, Aug. 1998, 23(15):1645-8.
Zeeman, R., et al., "Crosslinking and modification of dermal sheep collagen using 1,4-butanediol diglvcidyl ether," J Biomed Mater Res, 1999, 46:424-33.
Gratzer, Paul F., et al., "Control of pH Alters the Type of Crosslinking Produced by 1-Ethyl-3-(3-Dimethylaminopropyl)-Carbodiimide (EDC) Treatment of Acellular Matrix Vascular Grafts," J Biomed Mater Res, 2001, 58:172-179.
Tachibana, Akira et al., "Fabrication of wool keratin sponge scaffolds for long-term cell cultivation," Journal of Biotechnologv, 2002, 93:165-170.
Park, Si-Nae et al., "Characterization of porous collagen/hyaluronic acid scaffold modified by 1-theyl-3-(3-dimethylaminopropyl) carbodiimide crosslinking," Biomaterials, 2002, 23:1205-1212.
Billiar, Kristen et al., "Effects of carbodiimide crosslinking conditions on the physical properties of laminated intestinal submucosa," J Biomed Mater Res, 2001,56:101-108.

Zeeman, Raymond et al., "The kinetics of 1,4-butanediol diglycidyl ether crosslinking of dermal sheep collagen," J Biomed Mater Res, 2000, 51:541-548.

Zeeman, Raymond et al., "Successive epoxy and carbodiimide crosslinking of dermal sheep collagen," Biomaterials, 1999, 20:921-931.

Charulatha, V., et al., "Dimethyl 3,3'-dithiobispropionimidate: A novel crosslinking reagent for collagen," J. of Biomed. Mater Res., 2001, 54:122-128.

John, Annie et al., "A trial to prepare biodegradable collagen—hydroxyapatite composites for bone repair," J Biomater Sci Polymer Edn, 2001, vol. 12, No. 6, pp. 689-705.

Ueda, Hiroki et al., "Use of collagen sponge incorporating transforming growth factor-fβ1 to promote bone repair in skull defects in rabbits," Biomaterials, 2002, 23:1003-1010.

Sheu, Ming-Thau et al., "Characterization of collagen gel solutions and collagen matrices for cell culture," Biomaterials, 2001, 22:1713-1719.

Pieper, J.S. et al., "Development of tailor-made collagen-glycosaminoglycan matrices: EDC/NHS crosslinking, and ultrastructural aspects," Biomaterials, 2000,21:518-593.

Doillon, C.J., et al., "Collagen-based wound dressings: Control of the pore structure and morphology," J. of Biomed. Mater Res., 1986, 20:1219-1228.

Wissink, M.J.B. et al., "Immobilization of heparin to EDC/NHS-crosslinked collagen. Characterization and in vitro evaluation," Biomaterials, 2001, 22:151-163.

Wissink, M.J.B. et al., "Binding and release of basic fibroblast growth factor from heparinized collagen matrices," Biomaterials, 2001, 22:2291-2299.

Van Wachem, P.B. et al., "In vivo biocompatibility of carbodiimide-crosslinked collagen matrices: Effects of crosslink density, heparin immobilization, and bFGF loading," J Biomed Mater Res, 2001, 55:368-378.

Taguchi, Tetsushi et al., "An improved method to prepare hyaluronic acid and type II collagen composite matrices," J Biomed Mater Res, 2002,61:330-336.

Noah, Ernst Magnus et al., "Impact of sterilization on the porous design and cell behavior in collagen sponges prepared for tissue engineering," Biomaterials, 2002, 23:2855-2861.

Elbjeirami, Wafa M. et al., "Enhancing mechanical properties of tissue-engineered constructs via lysyl oxidase crosslinking activity," J Biomed Mater Res. 2003, 66A:513-521.

Schoof, Heike et al., "Control of Pore Structure and Size in Freeze-Dried Collagen Sponges." J Biomed Mater Res, 2001, 58:352-357.

Rocha, Lenaldo B., "Biocompatibility of anionic collagen matrix as scaffold for bone healing", Biomaterials, 2002, 23:449-456.

Progenix DBM Putty and Progenix Pllus (2009), Product Information from Medtronic. http://manuals.medtronic.eom/wcm/groups/mdtcomsg/@emanuals/@era/@spinal/documents/documents/wcmprod034012.pdf .downloaded on Feb. 12, 2010. p. 1-2.

Wang, et al., "A comparison of commercially available demineralized bone matrix for spainal fusion" Eur Spine J (2007) 16:1233-1240.

BIOSET™ DBM Distributed by Bone Bank Allografts, SteriGraft™, Manufactured by RTI Biologics, Inc., www.bonebank.com, 2009, product description, p. 44.

Grafton—Demineralized Bone Matrix (DBM), Osteotech, Inc. 2008, http:/www.graftondbm.com/grafton-matrix-strips.shtml, 1 pg.

* cited by examiner

BONE FILLER MATERIAL

CROSS-REFERENCE TO RELATED APPLICATIONS

This application is a continuation-in-part of U.S. application Ser. No. 12/695,925, filed Jan. 28, 2010, which is a continuation-in-part of U.S. application Ser. No. 11/415,036, filed May 1, 2006, the entirety of each of which is incorporated by reference.

BACKGROUND

The present invention relates generally to medical implants, more particularly, the present invention relates to osteoinductive medical products containing demineralized bone matrix.

A wide variety of implant formulations have been suggested in the art for the treatment of bone defects. In addition to traditional bone grafting, a number of synthetic bone graft substitutes have been used or explored, including some materials that contain demineralized bone matrix. Demineralized bone matrix has been shown to exhibit the ability to induce and/or conduct the formation of bone. It is thus desirable to implant and maintain demineralized bone matrix at a site at which bone growth is desired.

However, the beneficial nature of demineralized bone matrix is susceptible to disruption by the incorporation of incompatible materials or techniques when formulating the medical implant. At the same time, it is desirable to have implant products exhibiting good physical integrity to retain the demineralized bone matrix at the implant site, and that handle well in the operating environment and during implantation. As well, it is of considerable commercial significance that the formulation be manufacturable without undue cost, equipment or material burdens.

In view of the background in the area of demineralized bone matrix products, there exist a need for a product configuration that exhibits the ability to induce and/or support bone growth through the desired region and that has acceptable handling properties for surgeons.

Any publications or references discussed herein are presented to describe the background of the invention and to provide additional detail regarding its practice. Nothing herein is to be construed as an admission that the inventors are not entitled to antedate such disclosure by virtue of prior invention. Should there be a conflict, or apparent conflict, between the specification and any of the incorporated references, the specification takes precedence and the conflicting or apparently conflicting aspect of the reference is to be disregarded.

SUMMARY OF THE INVENTION

In an exemplary embodiment, the present invention provides a sheet-form demineralized bone matrix (DBM) product providing a bone growth scaffold for use in medical situations where bone regeneration is desired. The product comprises a resilient, porous sheet including DBM material and at least two binding agents selected from the group consisting of alginate, lecithin, pectin, gellan gum, starch, collagen and combinations thereof. The DBM particles are bound together using at least two binding agents without chemical cross-linking and the final form is made by dehydrating the product, such as by freeze drying or lyophilizing. The DBM material is thereby retained in the resilient, porous sheet and exhibits osteoinductivity.

In an exemplary embodiment, the present invention provides a sheet-form implant product providing a bone growth scaffold for use in medical situations where bone regeneration is desired. The product comprises a resilient, porous sheet including DBM material and/or cortical bone chips and/or cancellous bone chips and at least two binding agents selected from the group consisting of alginate, lecithin, pectin, gellan gum, starch, collagen and combinations thereof. The DBM or bone particles are bound together using at least two binding agents without chemical cross-linking and the final form is made by dehydrating the product, such as by freeze drying or lyophilizing. The DBM and/or bone particles (cancellous and/or cortical) are thereby retained in the resilient, porous sheet.

In another exemplary embodiment, the invention provides a pre-formed flexible bone graft extender or bone void filler. The product includes a three-dimensionally stable, yet flexible, porous implant structure which comprises DBM, alginate and at least one binding agent selected from the group consisting of lecithin, pectin, gellan gum, starch and collagen.

In another exemplary embodiment, the invention provides a pre-formed flexible bone graft extender or bone void filler. The product includes a dehydrated three-dimensionally stable porous implant structure, that becomes flexible following rehydration, which comprises DBM, alginate and at least one binding agent selected from the group consisting of lecithin, pectin, gellan gum, starch and collagen.

In another exemplary embodiment, the invention provides a pre-formed flexible bone graft extender or bone void filler possessing compression resistance in order to maintain space in a bone defect or cavity and allow regrowth of bone in the defect site or cavity.

In another exemplary embodiment, the invention provides a method for preparing a demineralized bone matrix (DBM) implant material. The method includes preparing an admixture including DBM, non-cross-linked alginate and at least one binding agent selected from the group consisting of lecithin, pectin, gellan gum, starch and collagen. An admixture of alginate, rehydrated DBM and at least one binding agent selected from the group consisting of lecithin, pectin, gellan gum, starch and collagen is prepared in a liquid medium to produce a homogeneous admixture at or below about 37° C. that may then be pored into a mold, freezing the DBM plus binder, and freeze drying the frozen DBM plus binder material, thereby yielding a pre-formed flexible bone graft extender or bone void filler having a pre-defined three-dimensional shape.

In another exemplary embodiment, the invention provides a method for preparing a demineralized bone matrix (DBM) implant material. The method includes preparing an admixture including DBM, non-cross-linked alginate, collagen and at least one binding agent selected from the group consisting of lecithin, pectin, gellan gum and starch. An admixture of alginate, collagen, rehydrated DBM and at least one binding agent selected from the group consisting of lecithin, pectin, gellan gum and starch is prepared in a liquid medium to produce a homogeneous admixture at or below about 37° C. that may then be pored into a mold and dehydrating the frozen DBM plus binder material, thereby yielding a pre-formed flexible bone graft extender or bone void filler having a pre-defined three-dimensional shape.

In another exemplary embodiment, the invention provides a method for preparing a demineralized bone matrix (DBM) implant material. The method includes providing an admixture including DBM and at least three binding agents selected from the group consisting of alginate, lecithin, pectin, gellan gum, starch and collagen in a liquid medium, with the DBM and binding agents present in a weight ratio of about 2.5:1 to about 5:1, about 1:1 to about 6:1 or about 1:1 to about 10:1 (dry weight). The composition may also include alginate and collagen in a weight ratio of about 0.5:1 to about 3:1, about 0.5:1 to about 2:1, about 0.5:1 to about 1.5:1, about 0.5:1 to about 1.25:1 or about 0.75:1 to about 1.25:1 (dry weight). The composition may also include a combination of alginate and collagen in a weight ratio relative to DBM (DBM:Alginate/collagen) of about 4:1 to about 7:1, about 3:1 to about 8:1, about 2:1 to about 10:1, or about 1:1 to about 12:1 (dry weight). The method may include the further steps of freezing the material to form a frozen precursor material, and/or drying the precursor material.

In another exemplary embodiment, the invention provides a method for preparing a demineralized bone matrix (DBM) implant material. The method includes providing an admixture including DBM particles, alginate, collagen and at least one additional binding agent selected from the group consisting of lecithin, pectin, gellan gum, and starch in a liquid medium at a temperature less than about 40° C. The admixture is then pored into a mold and dehydrated.

In another exemplary embodiment, the invention provides a method for preparing a demineralized bone matrix (DBM) implant material, wherein the method includes providing an admixture of alginate, collagen and at least one additional binding agent selected from the group consisting of lecithin, pectin, gellan gum, and starch in a aqueous medium, mixing the admixture to produce a homogeneous admixture, hydrating DBM particles, and combining the hydrated DBM particles with the homogeneous admixture, mixing the resulting composition at a temperature less than about 37° C., adding the resulting mixed composition to a mold and dehydrating the mixed composition, such as by freeze drying or lyophilizing the molded composition. In another exemplary embodiment, the invention provides a method for preparing a demineralized bone matrix (DBM) implant material, wherein the method includes providing an admixture of alginate and at least one additional binding agent selected from the group consisting of lecithin, pectin, gellan gum, and starch in a aqueous medium, mixing the admixture to produce a first solution, adding collagen to the first solution to produce a second solution, mixing the second solution to dissolve the collagen, hydrating DBM particles, and combining the hydrated DBM particles with the second solution to produce a third solution, mixing the third solution at a temperature less than about 37° C., adding the resulting mixed third solution to a mold and dehydrating the mixed third solution.

In still a further exemplary embodiment, the invention provides methods of treating a subject by implanting in a subject a DBM product as described herein, and provides kits comprising one or more DBM product described herein packaged in sterile condition. Optionally, instructions for use and/or instruments, such as a bone marrow aspiration needle, may be included.

In still a further exemplary embodiment, the invention provides methods of treating a subject comprising implanting in a subject a DBM product as described herein, wherein the DBM product has been pre-wetted with an aqueous solution, such as bone marrow aspirate, autograft, stem cells, saline, whole blood or a fraction of blood (e.g., a platelet or stem cell enriched fractions). The DBM product may be hydrated using either saline or bone marrow aspirate and can be used alone or with autograft to stimulate bone formation. Therefore, in another exemplary embodiment, the invention provides kits comprising one or more DBM product described herein packaged in sterile condition, optionally, also including instructions for use and/or additional instruments, such as a bone marrow aspiration needle. Optionally, the product may be packaged in a tray packaging configuration, wherein the inner tray may have cavities that hold the DBM product in place and a retainer configured to fit within the inner tray further securing the product within the inner tray. The kit may also comprise a foil lid sealing the inner tray. The inner tray may then be placed into an outer tray and sealed with a lid. The kit may then be placed into a carton that is subsequently sealed to prevent tampering and/or indicate a potential compromising of sterility. In an exemplary embodiment, the carton will have the product label printed thereon and may optionally have an e-beam sterilization indicator. In addition, the DBM product does not require temperature controlled shipping.

In still a further exemplary embodiment, the invention provides a DBM product substantially free of cortical cancellous bone chips, hyaluronic acid, glycosaminoglycans, chitosan, dentin, Calcium Sulfate, Calcium Carbonate, Ca Phosphate, a polymer exhibiting reverse phase behavior in an aqueous environment.

In yet another exemplary embodiment, the invention provides a DBM product that may be mixed with autograft, blood, blood derivatives, such as platelets and/or stem cells, bone marrow, bone marrow extract and bone marrow derivatives, such as platelets and/or stem cells. In yet another exemplary embodiment, the invention provides a DBM product that contains less than about 5%, about 4%, about 3%, about 2%, about 1%, about 0.5%, about 0.3% or about 0.1% residual calcium.

In yet another exemplary embodiment, the invention provides an implant fabricated from a DBM, alginate, collagen and at least one additional binding agent selected from the group consisting of alginate, lecithin, pectin, gellan gum and starch, wherein the implant retains a pre-defined shape for a period of time exceeding two months at room temperature and that has a substantially open pore structure that facilitates re-hydration with fluids, such as blood, autograft, allograft, bone marrow aspirate and/or mixtures and/or derivatives thereof.

In another exemplary embodiment, the invention provides a method of treating a bone defect in a subject comprising implanting a demineralized bone matrix (DBM) composition as described herein to a subject at a location at which bone growth is desired, and optionally adding a recombinant BMP protein or other therapeutic agent to the DBM composition and optionally administering a solution comprising a divalent cation to the DBM composition either before or after implanting the DBM composition.

Additional exemplary embodiments, as well as features and advantages thereof, will be apparent to those skilled in the art from the descriptions herein.

DETAILED DESCRIPTION OF THE INVENTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated product, and such further applications of the principles of the invention as described herein being contemplated as would normally occur to one skilled in the art to which the invention relates.

The uses of the terms "a" and "an" and "the" and similar references in the context of describing the invention (especially in the context of the following claims) are to be construed to cover both the singular and the plural, unless otherwise indicated herein or clearly contradicted by context.

As used herein, "biocompatible" means materials that do not induce undesirable long-term effects in vivo.

As used herein, "ratio of dry weight" means that the dry weight of two materials are compared in the absence of any solvent or solution, for example, a composition having 2.5 g DBM, 0.15 g alginate, 0.15 g gellan gum and 0.2 g collagen all added to 10 ml of water would have a DBM (2.5 g) to alginate and collagen (0.15 g+0.2 g=0.35 g) ratio of about 7:1 and would have a ratio of water to total dry weight of about 3.3:1.

Recitation of ranges of values herein are merely intended to serve as a shorthand method of referring individually to each separate value falling within the range, unless otherwise indicated herein, and each separate value is incorporated into the specification as if it were individually recited herein.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable medical products, and to methods for making and using the products. In particular embodiments, the osteoinductive medical implants are a three-dimensionally stable structure incorporating demineralized bone matrix (DBM) particles and at least two binding agents selected from the group consisting of alginate, lecithin, pectin, gellan gum, starch, and collagen. In other embodiments, the osteoinductive medical implants are a three-dimensionally stable structure incorporating demineralized bone matrix (DBM) particles and at least three binding agents selected from the group consisting of alginate, lecithin, pectin, gellan gum, starch, and collagen. In yet other embodiments, the osteoinductive medical implants are a three-dimensionally stable structure incorporating demineralized bone matrix (DBM) particles, alginate, collagen and at least one additional binding agent selected from the group consisting of lecithin, pectin, gellan gum and starch.

The term "demineralized bone matrix" refers to a matrix material prepared by demineralizing any bone source, including cortical and/or cancellous bone. Demineralized bone matrix materials may contain less than about 5% by weight of residual calcium, less than about 0.5% by weight of residual calcium or less than about 0.1% by weight of residual calcium. The source bone may be from any suitable source including autogenic, allogeneic, and/or xenogenic bone. When used in describing a demineralized bone matrix (DBM) material, the term "osteoinductive" refers to the ability of the DBM material to induce bone growth.

DBM materials may be obtained commercially or may be prepared by known techniques. In general, osteoinductive DBM materials may be prepared by decalcification of cortical and/or cancellous bone, often by acid extraction. This process may be conducted so as to leave collagen, noncollagenous proteins, and growth factors together in a solid matrix. Methods for preparing such bioactive DBM are well known, in respect of which reference can be made to U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. In certain embodiments, the particulate DBM material may have an average particle size of less than about 1,000 μm. For instance, the DBM material may have particle sizes in the range of 50 to 850 μm. DBM materials may be derived from human donor tissue, especially in regard to implant devices intended for use in human subjects.

Collagen may be collagen fibers which may optionally be populated with non-native cross-links, e.g. by chemical, dehydrothermal, radiation or other cross-linking techniques. Water soluble or insoluble collagen may be used, and may be derived from natural tissue sources (e.g. xenogenic, allogenic, or autogenic relative to the recipient human or other patient) or recombinantly prepared. See U.S. Patent Pub. 20070254041, incorporated by reference.

As noted above, the compositions of the invention include an amount of at least one binding agent, with the total amount of the at least one binding agent present in an amount less than that of the DBM on a weight-to-weight basis.

Heating of an intermediate solution may be carried out at any temperature desired and for any period of time desired, so long as the at least one binding agent and water enter into a homogeneous solution, the temperature range to be utilized may be from about 50° C. to about 180° C. However, addition of the DBM particles is preferably conducted when the solution has reached a temperature below about 40° C. or below about 37° C. The heating step may be conducted for any amount of time depending upon the temperature employed in the process, the concentration of additives (including one or more binding agents) and other factors.

In certain compositional embodiments of the invention, the product contains alginate, collagen, DBM, and at least one binding agent selected from the group consisting of lectin, pectin, gellan gum and starch, in a liquid medium. The composition may also be dehydrated.

In regard to the incorporated materials considered on a dry weight basis, the compositions of the invention may contain DBM material in an amount of between about 73% to about 83%, about 71% to about 85%, or about 65% to about 90%, based on dry weight. Likewise, a combination of alginate and collagen may be present in an amount between about 11% to about 17%, between about 10% to about 20%, or between about 5% to about 30%, based on dry weight. In addition, the formulation may have a total dry weight of compounds added to an aqueous solution, wherein the ratio of the aqueous solution (e.g., water, wherein 1 ml of $H_2O$=1 g for the purpose of determining the ratio herein) to the dry weight compounds is between about 1:1 to about 1:6, about 1:1 to about 1:4, about 1:1.5 to about 1:3.5, about 1:2 to about 1:3.5 or about 1:1.9 to about 1:3.3.

In certain aspects of the invention, medical implants are provided which comprise one or more starches that are noncross-linked. Starch may be obtained commercially and may be derived from sources including, but not limited to, cereal grain seeds (e.g., corn, wheat, rice, and sorghum), roots and tubers (e.g., potato), legumes and other sources. In an exemplary embodiment, the starch has a lower level of endotoxin than is typically found in commercially available starches.

In certain exemplary embodiments, the DBM material may be held together to form a three-dimensional implant without the use of any chemical cross-linker, such as glutaraldehyde, formaldehyde or a carbodiimide, to covalently link the one or more binding agents together.

Devices of the present invention may be manufactured in a ready-to-use condition and packaged in medically acceptable packaging in sterile condition, in either wet or dry formats. In some embodiments, the ready-to-use medical product may be a porous, sheet-form product, resembling a resilient sponge material. Sheet-form material configured as strips or other parallelepiped three dimensional bodies are readily manufactured, and provide beneficial products. The sheet-form product includes a first face, a second face, and four sidewalls interconnecting the first and second faces. The sheet-form product may have any suitable length (L), width (W) and thickness (T). In certain embodiments, the length (L) and width (W) will range from about 1 cm to about 50 cm, and the thickness T will range from about 0.1 cm to about 10 cm. More typically, the length and width will each range from about 1 cm to about 20 cm, and the thickness will be from about 0.2 cm to about 1 cm. From the standpoint of volume, preferred devices will have a body defining a volume of about 0.1 cm$^3$ to 500 cm$^3$, more typically in the range of about 1 cm$^3$ to about 100 cm$^3$, and most typically in the range of about 1 cm$^3$ to about 20 cm$^3$. It will be understood however that other linear and volumetric dimensions may also be employed within the scope of the present invention.

The bulk densities of the inventive devices may vary and depend upon factors such as the extent of their porosity, the densities of the incorporated materials, and the state of the device (e.g. hydrated or dehydrated condition). In certain embodiments, the device will be in a dried condition (containing less than 5% by weight of water or other liquid), and will have a bulk density in the range of about 0.1 g/cc to about 0.7 g/cc, about 0.1 g/cc to about 0.6 g/cc, about 0.1 g/cc to about 0.5 g/cc, about 0.1 g/cc to about 0.4 g/cc, about 0.1 g/cc to about 0.3 g/cc, or about 0.15 g/cc to about 0.25 g/cc. Nonetheless, as noted above these densities may vary with many factors, and bulk densities within these ranges, or that are lower or higher, may be exhibited by devices within aspects of the invention.

In some exemplary embodiments, the devices may be substantially porous. Devices may have a void volume of at least about 40% and typically in the range of about 40% to 90%. Moderate void volume levels of about 50% to less than 70%, or higher levels in the range of 70% to 90% or more, may be controllably achieved, for instance by varying the amount of water other aqueous liquids and/or porogens included in the formulation used to prepare the devices.

Devices may be manufactured by preparing a mixture including the DBM material, the one or more binding agents and an aqueous liquid to produce a homogeneous mixture. This mixture may then be placed in a mold, dehydrated, sterilized and packaged. Such drying advantageously utilizes lyophilization or other sublimation drying techniques that involve freezing the wet gel material and drying the material while frozen. In certain embodiments, the non-cross-linked admixture of materials is charged to a mold in a desired shape. The resultant shaped gel may be dried and potentially additionally processed to provide the device that is then packaged and sterilized as the final product.

The devices may be implanted in the patient in a dried or wetted condition. When wetted for use in a patient, any medically acceptable wetting agent may be used. These include, for example, aqueous substances such as sterile water, physiological saline, phosphate buffered saline, blood, bone marrow, bone marrow fractions or other liquid mediums, emulsions or suspensions that provide adequate wetting characteristics. Biocompatible organic liquids may also be used, alone or in combination with water. In desired forms, molecules of the wetting agent (e.g. water) will be taken up into the dried gelatin and starch matrix to form a wetted, firm gel device incorporating the particulate DBM material.

Implant devices of the invention may also contain other beneficial substances including for example preservatives, cosolvents, suspending agents, buffering agents (e.g. carrying active agents to be added to the device) viscosity enhancing agents, ionic strength and osmolality adjusters and/or other excipients.

The implant devices disclosed herein may also include other biocompatible and preferably bioresorbable substances. These materials may include, for example, natural polymers such as proteins and polypeptides, glycosaminoglycans, proteoglycans, elastin, hyaluronic acid, dermatan sulfate, or mixtures or composites thereof.

In another aspect of the invention, the devices may incorporate DBM particles having two distinct sizes, for example particles between about 2-4 mm in combination with smaller particles, for example, between about between about 210-710 µm.

Both human and non-human sources of bone are suitable for use in the instant invention, and the bone may be autographic, allographic or xenographic in relation to the mammal that is to receive the implant. Appropriate pre-treatments known in the art may be used to minimize the risks of disease transmission and/or immunogenic reaction when using such bone derived DBM particles.

Bioactive agents may be delivered with devices of the invention. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Bioactive agents may also be provided by tissue materials incorporated into the devices, including for instance autologous or allogenic tissue materials, which are incorporated into the material to be implanted in the patient. Such tissue materials may include blood or blood fractions, bone marrow or bone marrow fractions, and/or other sources of cells or other beneficial tissue components derived from the patient to be treated or another suitable animal source. These substances may, for example, be added to the device just prior to implantation into the patient.

Bioactive agents such as those described herein may be incorporated homogeneously or regionally into the implant devices by simple admixture, soaking or otherwise. The liquid phase of the medical implant compositions in accordance with certain aspects of the invention will comprise an amount of a polysaccharide, such as alginate. Preferred are ionic polysaccharides that are capable of forming thermally irreversible ionically-crosslinked gels upon combination with divalent or other polyvalent cationic materials. Suitable olysaccharides include, as examples, plant-derived polysaccharides such as alginates and pectins, and gel-forming derivatives thereof. Such ionic polysaccharides form ionically-crosslinked gels upon contact with aqueous solutions of counter-ions. For instance, useful agents for ionically crosslinking alginate and pectin polysaccharides include cationic gelling agents, preferably including divalent or trivalent cations. Useful divalent cations for these purposes include the alkaline earth metals, especially calcium and strontium. Aluminum is a useful cross-linking trivalent cation. These ionic cross-linking agents will usually be provided as salts. Useful anionic counter-ions for the calcium or other salts are desirably selected from pharmaceutically-acceptable anions such as chlorides, gluconates, fluorides, citrates, phosphates, tartrates, sulphates, acetates, borates, and the like. An especially preferred ionic cross-linking agent for use with an alginate or pectin compound is provided by calcium chloride. The cationic counter-ion may be any suitable, biocompatible or pharmaceutically-acceptable cation including for instance sodium, potassium, or ammonium. In an exemplary embodiment the cross-linking agent may be applied to the exterior of the DBM device just prior to implantation, in combination with implanting or following implantation. For example, the DBM device of the invention may be molded to a particular shape and implanted into a site in a subject thought to need enhanced bone growth and a solution containing a cation, such as calcium chloride, may be administered to the exposed surface of the implanted device, thereby producing an ionicly cross-linked film of alginate on the surface of the implanted device. For example, the DBM device may be molded to fit within a bone void and then some, or all, of the exterior surface may be contacted with a solution containing a cation, such as a divalent cation, e.g., calcium, for a relatively short period of time sufficient to form a thin partially cross-linked film on the exterior surface.

In certain embodiments, a device of the invention will include one or more substances, additional to the osteoinductive DBM material that induces or generates the formation of bone. Suitable osteogenic materials may include a growth factor that is effective in inducing formation of bone. Desirably, the growth factor will be from a class of proteins known generally as bone morphogenic proteins (BMPs), and may in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products thereof. These proteins may be used individually or in mixtures of two or more.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the device and particular protein being employed.

Other therapeutic growth factors or substances may also be used in devices of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

The osteogenic proteins or other biologically active agents, when used in the present invention, may be provided in liquid formulations, for example buffered aqueous formulations. In certain embodiments, such liquid formulations may be received upon and/or within, or otherwise combined with a dry-form device by a health care provider just prior to implantation. In other embodiments, such liquid formulations may be included within wet materials used to prepare a dry-form or wetted device during its manufacture. One suitable rhBMP-2 formulation is available from Medtronic Sofamor Danek, Memphis, Tenn., with its INFUSE® Bone Graft product.

Osteoinductive devices of the present invention may also comprise progenitor and/or stem cells derived from embryonic or adult tissue sources and/or taken from culture. Illustratively, compositions of the invention may incorporate cells derived from blood, bone marrow, or other tissue sources from the patient to be treated (autologous cells) or from a suitable allogenic or xenogenic donor source. In certain embodiments of the invention, the device incorporates an enriched bone marrow fraction, prepared for example as described in US Patent Publication No. 2005/0130301 to McKay et al. published Jun. 16, 2005, which is hereby incorporated herein by reference in its entirety. Thus, implantable materials may incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components may then be isolated from the separated sample, and incorporated into or onto a dry-form device of the invention, e.g. by using the fraction in or as a wetting medium applied to the device by a health care provider prior to implantation.

Osteoinductive devices of the present invention may also comprise suitable biostatic/biocidal agents including, but not limited to, antibiotics, povidone, sugars, mucopolysaccharides, chlorobutanol, quarternary ammonium compounds such as benzalkonium chloride, organic mercurials, parahydroxy benzoates, aromatic alcohols, halogenated phenols, sorbic acid, benzoic acid, dioxin, EDTA, BHT, BHA, TBHQ, gallate esters, NDGA, tocopherols, gum guaiac, lecithin, boric acid, citric acid, p-Hydroxy benzoic acid esters, propionates, Sulfur dioxide and sulfites, nitrates and nitrites of Potassium and Sodium, diethyl pyrocarbonate, Sodium diacetate, diphenyl, hexamethylene tetramine o-phenyl phenol, and Sodium o-phenylphenoxide, etc. When employed, biostatic/biocidal agent will typically represent from about 1 to about 25 weight percent of the bone particle containing composition, calculated prior to forming the shaped material. For example, the device may include one or more antibiotic drugs.

Osteoinductive devices of the present invention may also comprise suitable surface active agents, such as biocompatible nonionic, cationic, anionic and amphoteric surfactants and mixtures thereof. When employed, surface active agent will typically represent from about 1 to about 20 weight percent of the bone particle containing composition, calculated prior to forming the shaped material.

In still further embodiments, the present invention provides methods for treating patients that involve implanting in the patients an osteoinductive DBM device as described herein. In such uses, an osteoinductive DBM device may be implanted at a site at which bone growth is desired, e.g. to treat a bone disease, defect or location of trauma, and/or in some instances to promote artificial arthrodesis. The medical devices of the invention may be used as surgical implants at, in, on, or near bone defect sites, cartilage repair sites, or other musculoskeletal sites. In certain beneficial embodiments, the device will exhibit a conformable or flexible character that enables its introduction and shaping within voids, defects or other areas in which new tissue growth is desired, and/or in certain embodiments in which the delivery of a bioactive agent is desired. Further in this regard, the device may have compression-resistant properties sufficient to resist substantial compression when impinged by adjacent soft tissues of the body at a bony implant site, for instance at a posterolateral spinal fusion implant site.

Illustrative bone repair sites that may be treated with medical devices of the invention include, for instance, those resulting from injury, defects brought about during the course of surgery, infection, malignancy or developmental malformation. The devices may be used in a wide variety of orthopedic, periodontal, neurosurgical and oral and maxillofacial surgical procedures including, but not limited to: the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal cord tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones and/or metatarsal bones.

In accordance with certain aspects of the invention, the osteoinductive DBM device may be used as a bone void filler, or may be incorporated in, on or around load bearing implants such as spinal implants, hip implants (e.g. in or around implant stems and/or behind acetabular cups), knee implants (e.g. in or around stems). In inventive variants, the osteoinductive DBM devices may be incorporated in, on or around a load-bearing spinal implant device having a compressive strength of at least about 10000 N, such as a fusion cage, dowel, or other device potentially having a pocket, chamber or other cavity for containing the osteoinductive DBM device, and used in a spinal fusion such as an interbody fusion. One illustration of such use is in conjunction with a load-bearing interbody spinal spacer to achieve interbody fusion. In these applications, the device may be placed in and/or around the spacer to facilitate the fusion.

Illustrative cartilage repair sites that may be treated with devices of the invention include, but are not limited to, articular cartilage surfaces occurring in articular joints having at least two major bones. Examples include, but are not limited to the elbow, wrist, phalanx, knee, and ankle. Additionally, cartilage surfaces within shoulder and hip joints may be treated.

The present invention also provides medical kits and/or other products that include one or more osteoinductive DBM devices of the invention. Such products may include the device(s) of the invention, received in sterile condition in medical packaging. Such products may also include one or more additional surgical instruments or implants, for example a load-bearing implant (e.g. a spinal spacer), and/or a fluid transfer device such as a syringe, and/or a therapeutic substance, for example an osteogenic substance such as a BMP. In one specific form, such a medical kit may include a dried device of the invention, a BMP in lyophilized form (e.g. rhBMP-2), and an aqueous medium for reconstitution of the BMP to prepare an aqueous formulation that may then be added to the device.

The present invention also provides medical kits and/or other products that include one or more osteoinductive DBM devices of the invention. Such products may include the device(s) of the invention in a dried (e.g. having less than about 5% residual water), received in sterile condition in medical packaging. Such products may also include one or more additional surgical instruments or implants, for example a load-bearing implant (e.g. a spinal spacer), and/or a fluid transfer device such as a syringe, and/or a therapeutic substance, for example an osteogenic substance such as a BMP. In one specific form, such a medical kit may include a dried device of the invention, a BMP in lyophilized form (e.g. rhBMP-2), and an aqueous medium for reconstitution of the BMP to prepare an aqueous formulation of the BMP that may then be added to the dried device.

In an exemplary embodiment, the present invention provides a method of forming an osteoimplant, the method comprising: providing a mass of DBM particles in combination with one or more biocompatible components and/or multifunctional polymers. The DBM particles may initially be in the form of a powder, fibers, chips, or a combination thereof. The method may further comprise forming the final product as a flexible sheet. The method may also comprise shaping the final product using a press cutter to achieve a desired shape.

The invention will now be more particularly described with reference to the following specific examples. It will be understood that these examples are illustrative and not limiting of the embodiments of the invention.

EXAMPLE 1

| Reagents | Quantity |
| --- | --- |
| Alginate | 0.15 g |
| Gellan Gum | 0.15 g |
| Collagen | 0.2 g |
| DBM | 2.5 g |
| Water | 10 mls |

Sample Preparation Method:

2.5 g of DBM was measured out and rehydrated using a portion of the 10 mls of water. 0.15 g of alginate, 0.15 g of Gellan Gum and 0.2 g of Collagen were weighed out and hydrated with the remainder of the 10 mls of DI water. The rehydrated DBM was then mixed with the one or more binder solution to form a homogeneous final mixture. The final mixture was then poured into appropriately sized molds and frozen. The frozen products were then dried by lyophilization. The devices may then be sterilized & packaged.

EXAMPLE 2

| Reagents | Quantity |
| --- | --- |
| Alginate | 0.15 g |
| Collagen | 0.2 g |
| DBM | 2.0 g |
| Water | 8 mls |

Sample Preparation Method:

2.0 g of DBM was measured out and rehydrated using a portion of the 8 mls of water. 0.15 g of alginate and 0.2 g of Collagen were weighed out and hydrated with the remainder of the 8 mls of DI water. The rehydrated DBM was then mixed with the one or more binder solution to form a homogeneous final mixture. The final mixture was then poured into appropriately sized molds and frozen. The frozen products were then dried by lyophilization. The devices may then be sterilized & packaged.

EXAMPLE 3

| Reagents | Quantity |
| --- | --- |
| Alginate | 0.16 g |
| Gellan Gum | 0.30 g |
| Starch | 0.15 g |
| Collagen | 0.3 g |
| DBM | 2.5 g |
| Water | 10 mls |

Sample Preparation Method:

2.5 g of DBM was measured out and rehydrated using a portion of the 10 mls of water. 0.16 g of alginate, 0.3 g of Gellan Gum, 0.15 g starch and 0.2 g of Collagen were weighed out and hydrated with the remainder of the 10 mls of DI water. The rehydrated DBM was then mixed with the one or more binder solution to form a homogeneous final mixture. The final mixture was then poured into appropriately sized molds and frozen. The frozen products were then dried by lyophilization. The devices may then be sterilized & packaged.

EXAMPLE 4

| Reagents | Quantity |
| --- | --- |
| Alginate | 0.25 g |
| lectin | 0.25 g |
| Collagen | 0.2 g |
| DBM | 2 g |
| Water | 5 mls |

Sample Preparation Method:

As with the proceeding examples the rehydrated DBM was then mixed with the one or more binders in solution to form a homogeneous final mixture. The final mixture was then poured into appropriately sized molds and frozen. The frozen products were then dried by lyophilization.

EXAMPLE 5

| Reagents | Quantity |
| --- | --- |
| Alginate | 0.25 g |
| pectin | 0.15 g |
| Collagen | 0.2 g |
| DBM | 2 g |
| Water | 5 mls |

The sample was prepared as disclosed herein.

EXAMPLE 6

| Reagents | Quantity |
| --- | --- |
| Alginate | 0.25 g |
| pectin | 0.15 g |
| Gellan Gum | 0.15 g |
| Collagen | 0.2 g |
| DBM | 2 g |
| Water | 6 mls |

The sample was prepared as disclosed herein.

EXAMPLE 7

| Reagents | Quantity |
| --- | --- |
| Alginate | 0.15 g |
| Starch | 0.15 g |
| Collagen | 0.2 g |
| DI water | 8.0 ml |
| DBM | 2.0 g |

Sample Preparation Method:

2.0 g of DBM was measured out and rehydrated using a portion of the 8 mls of water. 0.15 g of alginate, 0.15 g of starch and 0.2 g of Collagen were weighed out and hydrated with the remainder of the 8 mls of DI water. The rehydrated DBM was then mixed with the one or more binder solution to form a homogeneous final mixture. The final mixture was then poured into appropriately sized molds and frozen. The frozen products were then dried by lyophilization.

EXAMPLE 8

Formulation Testing

Formulations are tested using athymic male rats. Samples are randomized so that no animal receives the same lot in both implant sites. The animals are anesthetized and prepared for surgery with pockets created in or between the muscle(s). The pockets are then filled with about 0.2 cc of the test article/sample and then the muscle pocket and skin are sutured closed. The animals are maintained in-life for 28 days.

At the end of the study duration, the animals are sacrificed and the implant site removed. Each implant is fixed, processed, and evaluated for histopathological evidence of new bone formation. Sections are taken from at least three levels of the test article within a block. The sections are mounted on slides for histological evaluation and a report is generated with scores for individual implant sites as either positive or negative relative to bone formation.

The Formulations in Examples 1 and 7 were Tested.

The formulations in Examples 1 and 7 herein were tested using athymic male rats. The implants were placed close to the femur but not touching the bone. In this study, explants were taken at the 4 week time point to determine the in vivo response to the implants.

The animals were anesthetized and prepared for surgery with pockets created in or between the muscle(s). The pockets were then filled with about 0.2 cc of the test article/sample and then the muscle pocket and skin were sutured closed.

At the end of the study duration, the animals were sacrificed and the implant site removed. Each implant was fixed, processed, and evaluated for histopathological evidence of new bone formation. Sections were taken from at least three levels of the test article within a block. The sections were mounted on slides for histological evaluation and a report was generated with scores for individual implant sites as either positive or negative relative to bone formation.

Both formulations were positive for bone formation.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are hereby incorporated by reference in their entirety.

What is claimed is:

1. A demineralized bone matrix (DBM) composition, comprising: an admixture of demineralized bone matrix (DBM) particles and at least one binding agent comprising alginate in an aqueous solvent; wherein the DBM particles are present in an amount of at least 65% by dry weight of the total dry weight of the composition; and wherein the admixture of demineralized bone matrix particles and at least one binding agent forms a three-dimensionally stable porous sheet material.

2. The DBM composition of claim 1, wherein greater than about 50% of the aqueous solvent is removed from the composition of claim 1 by evaporation.

3. The DBM composition of claim 1, wherein greater than about 75% of the aqueous solvent is removed from the composition of claim 1 by evaporation.

4. The DBM composition of claim 1, wherein the at least one binding agent further comprises collagen and at least one additional binding agent comprising starch.

5. The DBM composition of claim 4, wherein the combination of alginate and collagen are present in an amount between about 5% and about 30% by dry weight of the total dry weight of the composition.

6. The DBM composition of claim 4, wherein the ratio of DBM to the combination of alginate and collagen is about 2:1 by dry weight.

7. The DBM composition of claim 1, wherein the ratio of DBM to the at least one binding agent is about 2:1 by dry weight.

8. The DBM composition of claim 1, wherein the ratio of DBM to the at least one binding agent is between about 2:1 to about 5:1.

9. The DBM composition of claim 8, wherein the alginate and collagen are present in an amount of between 5% and about 30% by dry weight.

10. The DBM composition of claim 1, further comprising adding a recombinant BMP protein.

11. The DBM composition of claim 10, wherein the recombinant BMP protein is recombinant human BMP-2, recombinant human BMP-7 or recombinant human GDF-5.

12. The DBM composition of claim 1, wherein the admixture of demineralized bone composition particles and at least one binding agent is dehydrated.

13. The DBM composition of claim 1, containing no more than about 6% by weight water.

\* \* \* \* \*